| United States Patent [19] | [11] Patent Number: 4,803,190 |
| Sarumaru et al. | [45] Date of Patent: Feb. 7, 1989 |

[54] PROCESS FOR PRODUCTION OF COMPOSITE OXIDE CATALYSTS

[75] Inventors: Kohei Sarumaru; Etsuji Yamamoto, both of Ami, Japan

[73] Assignee: Mitsubishi Petrochemical Company Limited, Tokyo, Japan

[21] Appl. No.: 29,645

[22] Filed: Mar. 24, 1987

[30] Foreign Application Priority Data

Mar. 24, 1986 [JP] Japan ................... 61-65279

[51] Int. Cl.$^4$ .............. B01J 21/00; B01J 23/16; B01J 27/18
[52] U.S. Cl. .................. 502/205; 502/214; 502/249; 502/311
[58] Field of Search ........... 502/205, 249, 212, 214, 502/311

[56] References Cited

U.S. PATENT DOCUMENTS

| 3,173,957 | 3/1965 | McDaniel et al. | 502/249 |
| 3,806,470 | 4/1974 | Aykan et al. | 502/311 |
| 3,951,861 | 4/1976 | Shiraishi et al. | 502/249 |
| 4,409,127 | 10/1983 | Keppel et al. | 502/205 |
| 4,537,874 | 8/1985 | Sato et al. | 502/205 |

FOREIGN PATENT DOCUMENTS

| 083189 | 7/1983 | European Pat. Off. . |
| 2076288 | 10/1971 | France . |
| 2125047 | 9/1972 | France . |

*Primary Examiner*—Carl F. Dees
*Attorney, Agent, or Firm*—Oblon, Fisher, Spivak, McClelland & Maier

[57] ABSTRACT

In the production of a Mo-Bi-Na composite oxide catalyst by the process comprising incorporating compounds as respective element sources into a composite and subjecting the composite to heating treatment in an aqueous system, bismuth oxide and/or bismuth subcarbonate are/is used as a Bi source copmpound and at least a part of the heat treatment is conducted at a temperature of 450° to 600° C. The activity of the catalyst is significantly improved by introducing Bi in the form of the specified water insoluble compound into the catalyst.

10 Claims, No Drawings

PROCESS FOR PRODUCTION OF COMPOSITE OXIDE CATALYSTS

BACKGROUND OF THE INVENTION

1. Field of the Art

It is well known that Mo-Bi composite oxide catalysts are useful for selective reactions such as vapor phase catalytic oxidation reactions for producing acrolein from propylene or methacrolein from isobutene or tertiary-butanol, a vapor phase catalytic ammoxydation reaction for producing acrylonitrile from propylene or methacrylonitrile from isobutene, and a vapor phase catalytic oxidative dehydrogenation reaction for producing butadiene from butene. It is also well known that these catalysts have widely been put to practical use on an industrial scale.

2. Prior Art

Many patent publications with reference to the compositions of Mo-Bi oxide catalysts in these various reactions and the processes for producing them are also well known. A part of such publications are: Specifications of Japanese patent examined publication Nos. 3670/64, 4763/73, 3498/74, 17253/73, 1645/73, 41232/80, 14659/81, 23969/81, 52013/81 and 26245/82; and those of Japanese patent unexamined publication Nos. 503/73, 514/73, 52713/73, 57916/73, 54027/73, 76541/84, 47144/80, 20610/80, 84541/80 and 122041/85.

All of the aforementioned patent publications relate to Mo-Bi composite oxide catalysts. However, all but Japanese patent unexamined publication Nos. 47144/80 and 76541/84, which disclose the preliminary production of a Mo-Bi or W-Bi composite in the course of producing the composite oxide catalysts, use bismuth nitrate as a raw material of Bi in Examples, and in fact, a water soluble bismuth compound, viz. bismuth nitrate or a hydroxide thereof is recommended also in their descriptions.

It can be readily understood that when elements as the components of a composite oxide catalyst are incorporated into a composite by the use of a system including water as a dispersing medium, use of water soluble compounds as the compounds is the most common sense measure which one skilled in the art would conceive as a method for uniform dispersion in a catalyst. In fact, we have also confirmed that uniform dispersion of the compounds as aqueous solutions using such water soluble raw materials are effective in the case of the elements used for these composite oxides such as iron, cobalt, and nickel.

However, in the case of this composite oxide catalyst, it is not appropriate to use bismuth nitrate in a region having a high Bi content. The reason is that under conditions where bismuth nitrate is used, catalysts in the region having less Bi content are superior in their performance.

In Mo-Bi composite oxide catalysts, high Bi content is an important factor from the viewpoint of the catalyst life, and thus the above mentioned problem is serious.

SUMMARY OF THE INVENTION

This invention aims at improving catalyst properties by the use of a specified constituent element of Mo-Bi composite oxide catalysts, viz., Bi in a state of a nonhomogeneous system contrary to the aforementioned common sense.

In other words, there is provided, according to this invention, a process for producing a composite oxide catalyst, wherein a Mo-Bi composite oxide catalyst represented by the following formula is produced by a process in an aqueous system comprising incorporating the compounds as respective element sources into a composite and subjecting the composite to heat treatment, characterized in that bismuth oxide and/or bismuth subcarbonate are/is used as a Bi source and that heat treatment is conducted at 450°~600° C.:

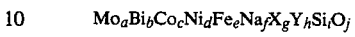
$$Mo_aBi_bCo_cNi_dFe_eNa_fX_gY_hSi_iO_j$$

wherein: X represents K, Rb, Cs and/or Tl; Y represents B, P, As and/or W; a–j represent atomic ratios, respectively, and when a equals 12, b=2–7, c=0–10, d=0–10, c+d=1–10, e=0.05–3, f=0–0.6, g=0.04–0.4, h=0–3, i=0–48 and j is a numeral which satisfies the oxidation states of the other elements.

Use of Bi in a non-homogeneous system from the viewpoint of the uniform dispersion of ingredient elements being counter to common sense of those skilled in the art, the catalyst properties of a Mo-Bi composite oxide catalyst was improved by employing such means.

In other words, a catalyst in a region having a high Bi content has excellent life as mentioned above. Thus, the process according to this invention can be said to be industrially valuable on the point that the reaction properties of the catalyst having the aforementioned properties, namely activity and selectivity, were remarkably improved without the aforementioned problem encountered in the use of bismuth nitrate. On the other hand, a process wherein a water soluble salt is not employed as a raw material does not exhibit any effect on the other elements, viz., iron, cobalt and nickel and only acts to lower the reaction performance of the catalyst.

The effect according to this invention depends on that Mo and Bi undergo thermal diffusion in a composite oxide solid phase in the course of heat treatment and form a bismuth molybdate compound, which can be described more fully as follows. A conventional method for using Bi is a technique for dissolving bismuth nitrate into an aqueous nitric acid solution, and thus under conditions where a large amount of Bi is used the system necessarily contains a large amount of nitrate groups. Then, when the solution which have been incorporated are evaporated to dryness, a complex salt which has been treated under strongly acidic conditions at very low pHs is formed. Such a composite oxide catalyst which has been passed through the complex salt formation process may be said to have a low performance. On the other hand, according to this invention, the oxides of Mo and Bi form a bismuth molybdate compound by thermal diffusion without passing through the process of the complex salt formation, and thus there is a possibility of forming a composite oxide catalyst having high performance. Moreover, it is estimated that such a composite oxide catalyst as produced by a thermal diffusion technique may form a certain kind of lattice defect.

DETAILED DESCRIPTION

Catalyst

Basic catalyst

The Mo-Bi composite oxide catalysts according to this invention are essentially identical to the conventional ones (e.g., those described in the aforementioned patent publications) except that the compound as a Bi source is specified.

Therefore, the Mo-Bi composite oxide catalysts according to this invention can be represented typically by the following formula. The formula is usually used for the expression of composite oxide catalysts and does not necessarily mean the presence of a sole compound represented by this chemical formula.

$$Mo_aBi_bCo_cNi_dFe_eNa_fX_gY_hSi_iO_j$$

wherein: X represents K, Rb, Cs and/or Tl; Y represents B, P, As and/or W; and suffixes of respective elements represent their atomic ratios of the following values.
a: 12,
b: 2 to 7,
c: 0 to 10
d: 0 to 10,
c+d: 1 to 10,
e: 0.05 to 3,
f: 0 to 0.6,
g: 0.04 to 0.4,
h: 0 to 3,
i: 0 to 48 and
j: values satisfying the oxidation degree of other elements.

Production of catalyst

The process for production of the catalysts is essentially identical to the conventional ones except for the consideration on the kinds (and embodiments of application) of the compounds as Bi sources.

The production of the Mo-Bi composite oxide catalysts generally comprises incorporating the compounds as respective element sources into a composite and subjecting the composite to heating in an aqueous system.

The phraseology "incorporating the compounds as respective element sources into a composite in an aqueous system" means incorporating aqueous solutions or aqueous dispersions of respective compounds simultaneously or stepwisely into a composite. The term "compounds as respective element sources" means not only respective compounds for each of the elements but also includes the compounds containing a plurality of elements (e.g., ammonium phospho-molybdate for Mo and P). The term incorporating means not only incorporating the compounds as respective element sources into a composite but, if necessary, includes the case of incorporating carrier materials such as silica, alumina, silica-alumina, refractory oxides or other materials.

On the other hand, the "heating" aims at the formation of individual oxides and/or composite oxides of the compounds as respective element sources and the thermal treatment of the finally produced composite oxides. The target of the heating is primarily the compounds as respective element sources, but the compounds may be other than the composite of the compounds as all of the element sources. The heating is not necessarily limited to only once. Therefore, the term "heating" used in this specification includes also the case where heating is carried out for each of the compounds as respective element sources, and the formation (and, if necessary, the formation of composite oxides) is carried out stepwisely. The phraseology "comprises incorporating and subjecting to heating" means that suitable processes such as drying, grinding, molding and the like in addition to these two processes may be carried out.

According to this invention, the compounds as Bi sources are water insoluble bismuth oxide and/or bismuth subcarbonate. The compound is preferably used in the form of powder. The compound as a raw material for producing the catalyst may be particles of particle size larger than powder, but the smaller particles are preferred in order to carry out the heating process for the thermal diffusion thereof. Therefore, if these compounds as the raw materials are not particles of small size, pulverization should be conducted prior to heat treatment.

A specific example of the process for producing the catalyst according to this invention will now be described. The aforementioned patent publications and the like are now well known in the art, and thus conception of other examples by inference from this specific example should be easy for those skilled in art.

To an aqueous solution of a molybdenum compound, preferably ammonium molybdate are added aqueous solutions of iron, cobalt and nickel, preferably nitrates thereof. Further, the compounds of sodium, potassium, rubidium, thallium, boron, phosphorus, arsenic and/or tungsten, preferably water soluble salts thereof are added as aqueous solutions thereof. Furthermore, if necessary, particulate or colloidal silica is added. Then, bismuth oxide and/or bismuth subcarbonate are added in a form of powder. Slurry thus obtained is amply agitated and then dried. The dry product in the form of granules or cake is subjected to heat treatment in a short period at a temperature in the range of 270° to 350° C. to form an oxide.

It has been found from analyses by X-ray diffraction method and Raman spectrometry that, in the heat treated product thus obtained, iron, cobalt and nickel have already formed salts with acidic oxides, but bismuth still remains in the form of the raw material. The decomposition product thus obtained is formed into a desired shape by a method such as extrusion molding, tableting molding, carrying molding or the like.

Next, the product is subjected to final thermal treatment at a temperature condition of 450° to 650° C. for 1 to 16 hours to obtain a catalyst.

It is presumed that an important aspect of this invention is the reaction which is caused in the course of the final heat treatment. On estimating the contents occurring in the course of this heat treatment, cobalt and nickel have already formed molybdate salts, respectively and the other compounds also form dispersed composite oxides before the heat treatment. However, a part of molybdenum (usually added in an amount in excess of that required for forming the aforementioned compound) and bismuth do not form salts yet and form oxides and/or carbonates, respectively. It may be considered that when the composite oxide is subjected to heat treatment in the final step, molybdenum and bismuth diffuse to each other, and thus a bismuth molybdate phase contacting with the surface of the molybdate salt which primarily comprises iron, cobalt and nickel is formed homogeneously. In this case, it is believed that iron, nickel and cobalt are never solid-dissolved into the bismuth molybdate phase.

The temperature condition in this final heat treatment is very important because it is difficult to obtain a sufficient diffusion speed at a temperature less than 450° C., and an extremely long period is disadvantageously required for the homogeneous dispersion.

It is lso disadvantageous that at a temperature exceeding 650° C., a part of the molybdate salt is sintered, and thus the specific surface area of the catalyst is extensively reduced. Therefore, the preferable heating temperature is in the range of 450° to 650° C. The heating period is 1 to 10 hours. The heating atmosphere in this case is non-reducible, preferably in the presence of molecular oxygen, particularly in air.

Use of catalyst

The composite oxide catalysts according to this invention can be used for various vapor phase catalytic oxidation reactions carried out in the presence of molecular oxygen.

The examples of the vapor phase catalytic oxidation reaction mentioned in this specification include the reaction for producing acrolein or methacrolein from propylene, isobutene or t-butanol, the reaction for producing acrylonitrile or methacrylonitrile from propylene or isobutene in the presence of ammonia, and the reaction for producing butadiene from butene and the like.

EXPERIMENTAL EXAMPLES

Example 1

In 400 ml of pure water is dissolved 94.1 g of ammonium paramolybdate under heating. Next, 7.18 g of ferric nitrate and 51.7 g of nickel nitrate are dissolved in 60 ml of pure water under heating. These two solutions are slowly mixed with each other by ample agitation. Then, 0.85 g of borax is dissolved in 40 ml of pure water, and the solution is added to the above-mentioned slurry. Next, 33.4 g of particulate silica ("CARPLEX") and 51.7 g of bismuth oxide are added, and the mixture is agitated well and then evaporated to dryness. The solid body thus obtained is subjected to heat treatment under aerial atmosphere at 300° C. for 1 hour into an oxide. The solid body is formed into tablets of 5 mm in diameter and 4 mm in height by the use of a small scale molding machine and then calcined in a muffle furnace at 500° C. for 4 hours to obtain a catalyst.

The composition of the catalyst calculated from the raw materials charged are illustrated by the composite oxide catalyst having the following atomic ratios.

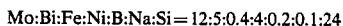

Mo:Bi:Fe:Ni:B:Na:Si=12:5:0.4:4:0.2:0.1:24

This catalyst in an amount of 40 ml is charged into a stainless steel reaction tube having an internal diameter of 15 mm, and oxidation reaction of propylene is carried out by passing the raw material gas comprising 10% of propylene concentration, 17% of steam concentration and 73% of air concentration through the tube with a contact period of 4.8 seconds under atmospheric pressure.

At a reaction temperature of 290° C., the following results of reaction were obtained in an actual instance of practice.
Conversion of propylene: 95.4%
Yield of acrolein: 80.8%
Yield of acrylic acid: 7.8%
Total yield: 88.6%

Comparative Example 1

A catalyst having the same composition as in Example 1 was produced under the conditions in Example 1 except that an aqueous solution in which 108 g of bismuth nitrate had been dissolved in 98 ml of pure water to which 12 ml of nitric acid had been added was used in place of the bismuth oxide used as a raw material of Bi in Example 1.

Using this catalyst, oxidation reaction of propylene was carried out under the same reaction conditions as in Example 1. The results obtained at a reaction temperature of 290° C. were as follows.:
Conversion of propylene 82.6%
Yield of acrolein 66.2%
Yield of acrylic acid 6.9%
Total yield 73.1%

Example 2

In 400 ml of pure water is disolved 94.1 g of ammonium paramolybdate under heating. Next, 7.18 g of ferric nitrate, 25.8 g of cobalt nitrate and 38.7 g of nickel nitrate are dissolved in 60 ml of pure water under heating. These two solutions are slowly mixed with each other by ample agitation.

To the mixed solution (slurry) is added a solution in which 0.85 g of borax, 0.38 g of sodium nitrate and 0.36 g of potassium nitrate have been dissolved in 40 ml of pure water under heating, and the mixture is amply agitated. Then, 57.8 g of bismuth subcarbonate and 64 g of silica are added to the mixture and mixed with agitation. Next, after heat drying of the slurry, it is subjected to thermal treatment at 300° C. for 1 hour in an aerial atmosphere. The solid body thus obtained is formed into tablets of 5 mm in diameter and 4 mm in height by the use of a small scale molding machine and then calcined in a muffle furnace at 480° C. for 8 hours to obtain a catalyst. The composition ratios of the metal ingredients of the catalyst calculated from the raw materials charged are illustrated by the composite oxide having the following atomic ratios.

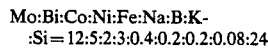

Mo:Bi:Co:Ni:Fe:Na:B:K:Si=12:5:2:3:0.4:0.2:0.2:0.08:24

Using this catalyst in an actual instance of practice, oxidation reaction of propylene was carried out in the same reactor as in Example 1 by passing the raw material gas comprising 12% of propylene concentration, 10% of steam concentration and 78% of air concentration through the reactor with a contact period of 4.2 seconds at a usual pressure.

At a reaction temperature of 290° C., the following results of reaction were obtained.
Conversion of propylene 98.5%
Yield of acrolein 89.7%
Yield of acrylic acid 5.1%
Total yield 94.8%

Comparative Example 2

A catalyst having the same composition as of the one in Example 2 was produced under the conditions in Example 2 except that an aqueous solution in which 108 g of bismuth nitrate had been dissolved in 98 ml of pure water to which 12 ml of nitric acid had been added was used in place of the bismuth subcarbonate used as a raw material of Bi in Example 2.

Using this catalyst, oxidation reaction of propylene was carried out under the same reaction conditions as in Example 2. The results obtained at a reaction temperature of 290° C. were as follows:
Conversion of propylene 97.2%
Yield of acrolein 88.0%
Yield of acrylic acid 4.1%
Total yield 92.1%

Example 3

In 400 ml of pure water is disolved 94.1 g of ammonium paramolybdate under heating. Next, 5.8 g of ammonium paratangstate is added, and the mixture is agitated.

Then, 17.9 g of ferric nitrate, 51.7 g of cobalt nitrate, 0.38 g sodium nitrate, 0.85 g of borax and 0.27 g of potassium nitrate are dissolved in 100 ml of pure water. These two solutions are slowly mixed with each other by ample agitating. Then, to the mixed solution are added 62.0 g of bismuth oxide and 64.0 g of silica, and mixture is mixed with agitation. In an actual instance of practice, a catalyst was produced in the same operations as in Example 1.

The composition of the catalyst calculated from the raw materials charged is illustrated by the following atomic ratios for the metal ingredients of the composite oxide.

Mo:Bi:Fe:Co:W:B:Na:K:Si=12:6:1:4:0.5:0.2:0.2:0.06:24

Using this catalyst, oxidation reaction of propylene was carried out in the same manner as in Example 2.

The following results were obtained at a reaction temperature of 290° C.
Conversion of propylene 98.0%
Yield of acrolein 88.9%
Yield of acrylic acid 4.8%
Total Yield 93.7%

Example 4

In 400 ml of pure water is dissolved 94.1 g of ammonium paramolybdate under heating. Next, 7.18 g of ferric nitrate, 25.8 g of cobalt nitrate and 38.7 g of nickel nitrate are dissolved in 60 ml of pure water under heating. These two solutions are slowly mixed with each other by ample mixing.

To the mixed solution (slurry) is added a solution in which 0.85 g of borax, 0.38 g of sodium nitrate and 0.36 g of potassium nitrate have been dissolved in 40 ml of pure water under heating, and the mixture is amply agitated. Then, 51.7 g of bismuth oxide and 64 g of silica are added to the mixture and mixed with agitation. Next, after heat drying of the slurry, it is subjected to thermal treatment at 300° C. for 1 hour in an aerial atmosphere. The solid body thus obtained is formed into tablets of 5 mm in diameter and 4 mm in height by the use of a small scale molding machine and then calcined in a muffle furnace at 500° C. for 4 hours to obtain a catalyst. The composition ratios of the metal ingredients of the catalyst calculated from the raw materials charged are illustrated by the composite oxide having the following atomic ratios.

Mo:Bi:Co:Ni:Fe:Na:B:K:Si=12:5:2:3:0.4:0.2:0.2:0.08:24

By using this catalyst, in an actual instance of practice, ammoxydation reaction of propylene was carried out in the same reactor as in Example 1 by passing the raw material gas comprised 4.3% of propylene concentration, 10.1% of ammonia concentration, 34.2% of steam concentration and 51.9% of air concentration through the reactor with a contact period of 2.9 seconds under atmospheric pressure.

At a reaction temperature of 330° C., the following results of reaction were obtained.

Conversion of propylene 58.3%
Yield of acrylonitrile 48.7%
Selectivity of acrylonitrile 83.5%

Comparative Example 3

A catalyst having the same composition as of the one in Example 4 was produced under the conditions in Example 4 except that an aqueous solution in which 108 g of bismuth nitrate had been dissolved in 98 ml of pure water to which 12 ml of nitric acid had been added was used in place of the bismuth oxide used as a raw material of Bi in Example 4.

By using this catalyst, ammoxydation reaction of propylene was carried out under the same reaction conditions as in Example 4. The results obtained were as follows:
Conversion of propylene 47.7%
Yield of acrylonitrile 40.8%
Selectivity of acrylonitrile 85.7%

What is claimed is:

1. A process for producing a composite oxide catalyst, wherein a Mo-Bi composite oxide catalyst represented by the following formula is produced by a process in an aqueous system comprising incorporating the compounds as respective element sources into a composite and subjecting the composite to heat treatment, characterized in that bismuth oxide and/or bismuth subcarbonate substantially insoluble in said aqueous system is used as a Bi source and that heat treatment is conducted at 450° to 600° C.;

$$Mo_aBi_bCo_cNi_dFe_eNa_fX_gY_hSi_iO_j$$

wherein: X represents K, Rb, Cs and/or Tl; Y represents B, P, As and/or W; a through j represent atomic ratios, respectively, and, when a equals 12, b=2 to 7, c=0 to 10, d=0 to 10, c+d=1 to 10, e=0.05 to 3, f=0 to 0.6, g=0.04 to 0.4, h=0 to 3, i=0 to 48 and j is a numeral which satisfies the oxidation states of the other elements.

2. A process according to claim 1, wherein the bismuth oxide and/or bismuth subcarbonate are/is used in a form of powder.

3. A process according to claim 1, wherein prior to the said heat treatment at a temperature of 450° to 600° C., said composite is heated in air and at least the greater part of the compounds as respective element sources are decomposed into a composite oxide.

4. A process according to claim 3, wherein the composite oxide subjected to heat treatment at a temperature of 450° to 600° C. is in the shape desired for the catalyst.

5. A process according to claim 1, wherein heat treatment at a temperature of 450° to 600° C. is conducted in a non-reducible atmosphere.

6. The composite oxide catalyst prepared by the process of claim 1.

7. The composite oxide catalyst prepared by the process of claim 2.

8. The composite oxide catalyst prepared by the process of claim 3.

9. The composite oxide catalyst prepared by the process of claim 4.

10. The composite oxide catalyst prepared by the process of claim 5.

* * * * *